United States Patent [19]
Howe

[11] Patent Number: 5,617,847
[45] Date of Patent: Apr. 8, 1997

[54] ASSISTED BREATHING APPARATUS AND TUBING THEREFORE

[76] Inventor: Stephen L. Howe, 5829 E. Bloomfield Rd., Scottsdale, Ariz. 85254

[21] Appl. No.: 542,070

[22] Filed: Oct. 12, 1995

[51] Int. Cl.$^6$ .................................................. A61M 16/00
[52] U.S. Cl. ................................ 128/204.23; 128/205.19; 128/911; 128/912
[58] Field of Search ...................... 128/204.23, 204.26, 128/205.19, 911, 912, 202.27

[56] References Cited

U.S. PATENT DOCUMENTS

| | | | |
|---|---|---|---|
| 4,007,737 | 2/1977 | Paluch | 128/911 |
| 4,538,604 | 9/1985 | Usry et al. | 128/911 |
| 4,621,634 | 11/1986 | Nowacki et al. | 128/911 |
| 4,637,384 | 1/1987 | Schroeder | 128/911 |
| 4,676,239 | 6/1987 | Humphrey | 128/911 |
| 4,967,744 | 11/1990 | Chua | 128/911 |
| 5,033,464 | 7/1991 | Delcastilho | 128/205.19 |
| 5,040,529 | 8/1991 | Zalkin | 128/204.26 |
| 5,121,746 | 6/1992 | Sikora | 128/912 |
| 5,127,400 | 7/1992 | DeVries et al. | 128/204.23 |
| 5,284,160 | 2/1994 | Dryden | 128/911 |

FOREIGN PATENT DOCUMENTS 317417  5/1989  European Pat. Off. .......... 128/204.23

Primary Examiner—Aaron J. Lewis
Attorney, Agent, or Firm—Warren F. B. Lindsley

[57] ABSTRACT

A tubing assembly is disclosed for use between an exhalation valve and a ventilator for providing assisted breathing to a patient. The ventilator has a patient air outlet, a exhalation valve control outlet and a sensor outlet connected to a sensing mechanism. The exhalation valve has a first outlet to a tracheotomy connector, a second outlet to ambient atmosphere, an inlet and a control air inlet. The exhalation valve is switched between an inhalation position and an exhalation position by air pressure at the control air inlet. The tubing assembly comprises an exhalation valve connection, a ventilator-sensor connection, an intermediate tube, a sensor tube and an exhalation valve control tube assembly. The exhalation valve connection is attached at one end to the intermediate tube and at the other end to the inlet. The ventilator-sensor connection is attached at one end to the patient air outlet and at the other end to the intermediate tube. The sensor tube is connected at one end to the ventilator-sensor connection and at the other end to the sensor outlet. The exhalation valve control tube assembly is connected at one end to the control air inlet and at the opposite end to the exhalation valve control outlet whereby the ventilator controls the air pressure at the control air inlet. The exhalation valve control tube assembly extends through the exhalation valve connection, through the intermediate tube and through the ventilator-sensor connection.

4 Claims, 2 Drawing Sheets

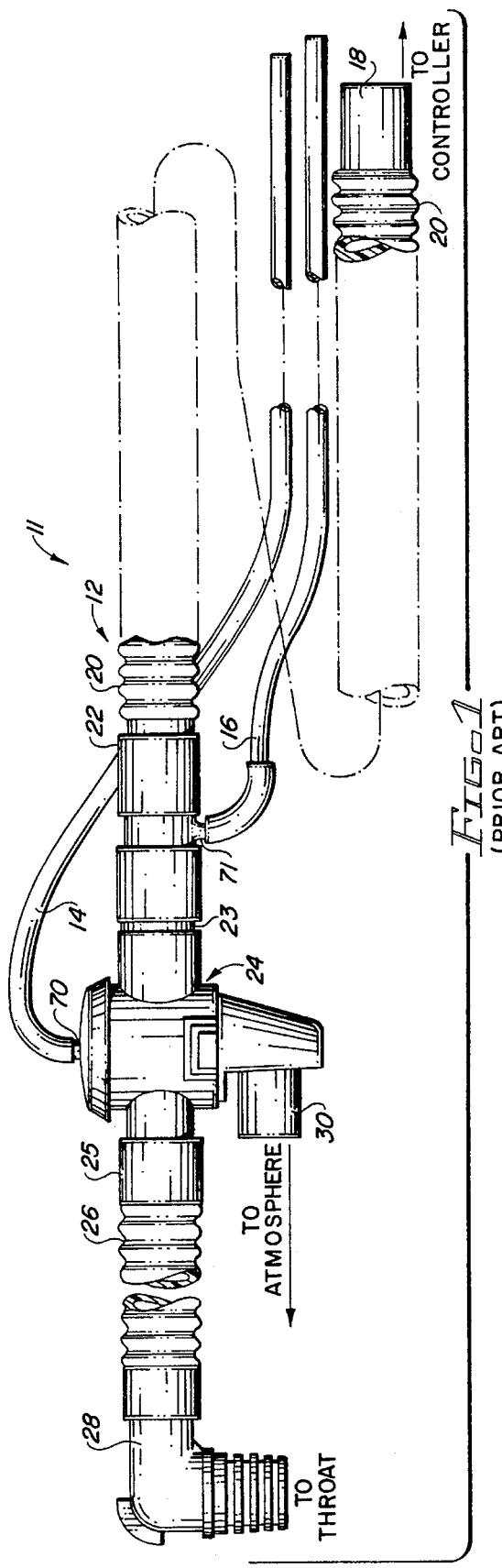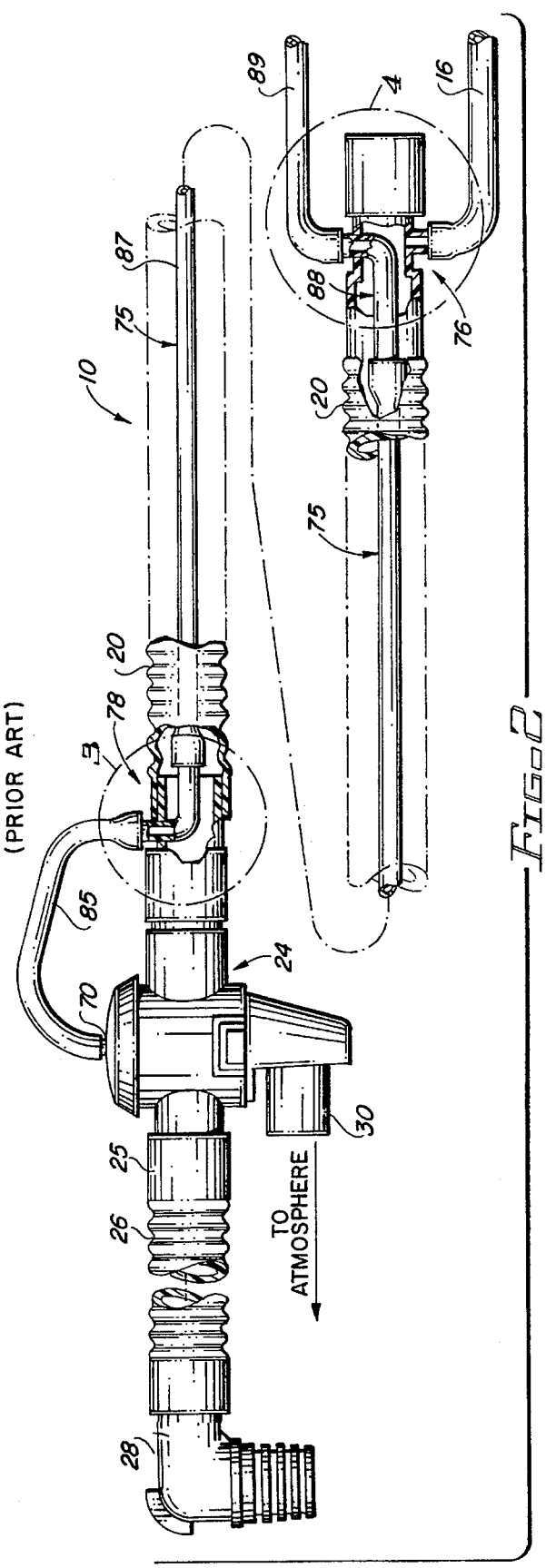

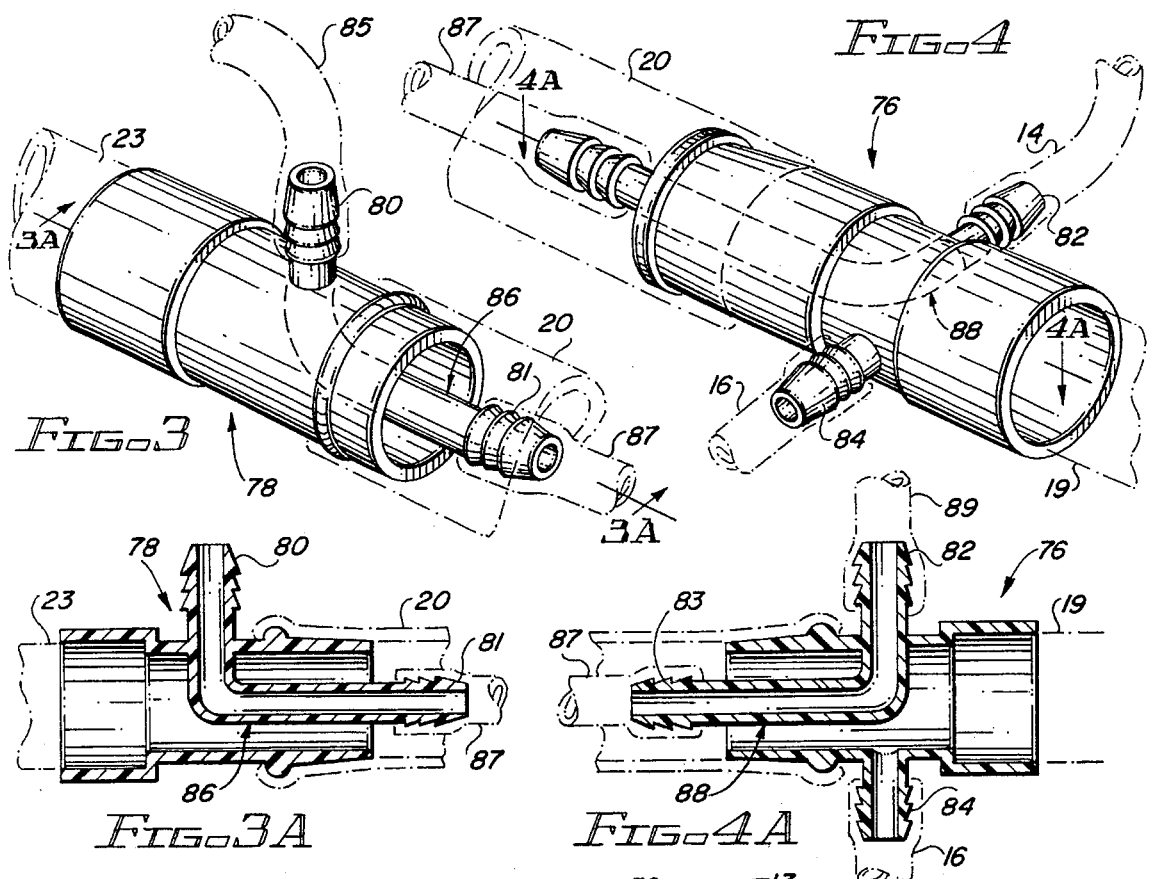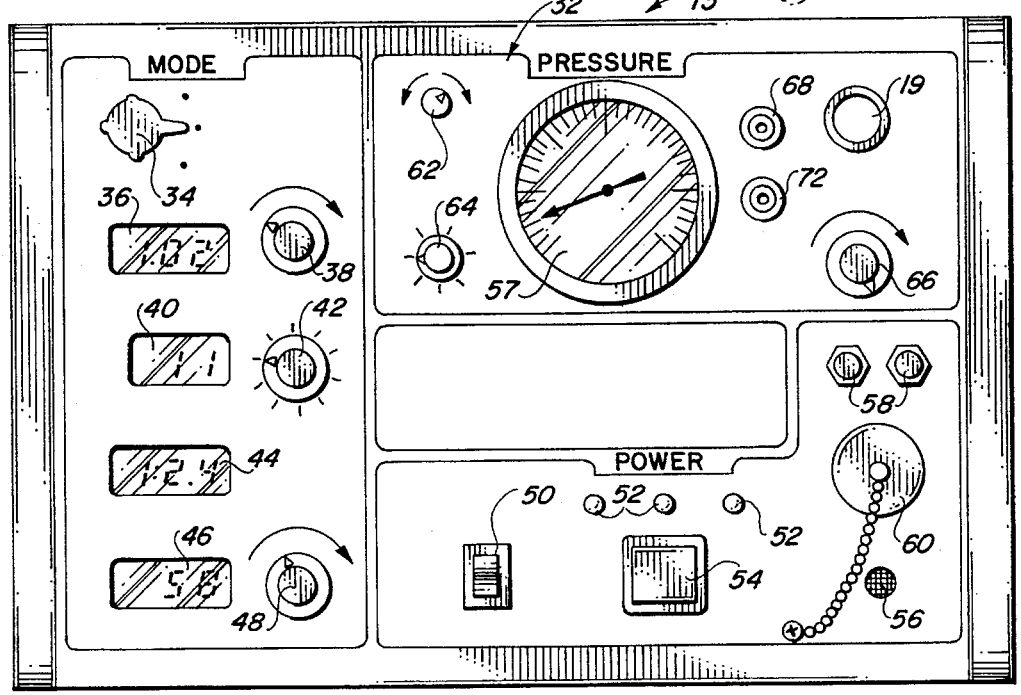

ASSISTED BREATHING APPARATUS AND TUBING THEREFORE

BACKGROUND OF THE INVENTION

This invention relates to an apparatus which is used to assist individuals in breathing after tracheotomy surgery, and, more particularly, to tubing used in connection with such apparatus.

At present, many individuals who have had tracheotomy surgery require assistance in breathing. Such assistance may be temporary or permanent depending on the individual's condition. In either event, apparatus used to assist breathing should be portable, safe and easy to use.

DESCRIPTION OF THE PRIOR ART

Present apparatus used to assist individuals in breathing are generally comprised of a control mechanism which forces air into a patient's throat and, hence, lungs. The mechanism controls the inspiratory and expiratory cycles via air pressure directed through a plurality of separate tubes. The entire apparatus is lightweight and portable.

The known prior art is described above and further explained below. None of the known prior art disclose the device set forth herein.

SUMMARY OF THE INVENTION

In accordance with the invention claimed, one object of this invention is to provide an improved portable, safe and easy to use apparatus for assisting individuals in breathing after a tracheotomy.

It is another object of this invention to provide an easy to use tubing assembly for use in connection with existing assisted breathing apparatuses.

Further objects and advantages of the invention will become apparent as the following description proceeds and the features of novelty which characterize this invention will be pointed out with particularity in the claims annexed to and forming part of this specification.

BRIEF DESCRIPTION OF THE DRAWINGS

The present invention may be more readily described by reference to the accompanying drawings, in which:

FIG. 1 is a side view of the tubing assembly of the prior art;

FIG. 2 is a side view of the tubing assembly of the present invention;

FIG. 3 is a perspective view of a connector used in the present invention and designated by the numeral 3 in FIG. 2;

FIG. 3A is a cross sectional view of the connector of FIG. 3 taken along line 3A—3A;

FIG. 4 is a perspective view of a second connector used in the present invention and designated by the numeral 4 in FIG. 2;

FIG. 4A is a cross sectional view of the second connector of FIG. 4 taken along line 4A—4A; and FIG. 5 shows a ventilator used with the present invention.

DESCRIPTION OF THE PREFERRED EMBODIMENT

In accordance with the invention claimed, FIGS. 2–4 disclose an assisted breathing apparatus and tubing assembly 10 of the present invention. FIG. 1 shows the tubing assembly 11 used in the prior art. FIG. 5 shows a control panel 32 of a ventilator 13 which is used with both the prior art and the present invention. Ventilator 13 includes a volume air pump which is used to provide air to patients as needed.

As shown in FIG. 1, the prior art tubing assembly 11 comprises an air tube 12, an exhalation valve control tube 14 and a sensor tube 16. As illustrated, each tube 12, 14 and 16 is of a different size to prevent inadvertently connecting said tubes incorrectly. Air tube 12 comprises a ventilator connection 18 which connects at one end to the air pump of ventilator 13 via a patient air outlet 19 and at a second end to an intermediate tube 20, an exhalation valve-sensor connection 22 which connects to intermediate tube 20 at one end and to an inlet 23 of an exhalation valve 24 at the opposite end, a second intermediate tube 26 connected at one end to a first outlet 25 of exhalation valve 24 to a tracheotomy connector 28 at the opposite end.

Turning now to FIG. 5, a control panel 32 of ventilator 13 is shown. The illustrated panel 32 is an actual Model PLY-100 ventilator available from Lifecare International, Inc. of Westminster, Colo. Those skilled in the art will understand that ventilators made by other entities can be employed with the present invention.

Ventilator 13 can be operated in three separate modes set by mode switch 34. The modes range from a control mode which completely controls the patient's breathing to a mode dependent upon the patient's own inspiratory effort and respiratory drive as well as an intermediate mode with some patient control.

Control panel 32 includes a tidal volume display 36 and tidal volume control knob 38. Tidal volume can be set by knob 38 to range from 50 milliliters to 3000 milliliters of air. Display 36 shows the tidal volume of air at the patient air outlet.

A respiratory rate display 40 and associated respiratory rate dial 42 show and control the respiratory rate of a patient. The rate can be set anywhere from 2 to 40 breaths per minute.

An I/E ratio display 44 shows the ratio of the inspiratory time to the expiratory time. I/E ratio display 44 will alarm by flashing if the inspiratory time is greater than the expiratory time or if the ratio exceeds 1:9.9.

An inspiratory flow rate display 46 and an associated flow rate control 48 show and alter, respectively, the peak flow of gas in the inspiratory phase of respiration. The flow rate can be adjusted between 10 and 120 liters per minute to accommodate both adults and children. A rocker switch 50 allows this flow rate display 46 to double as a voltage indicator when the unit operates under either internal or external DC (battery) power. When the inspiratory flow rate is too low to accomplish the tidal volumes and respiratory rates desired, the display also visually alarms.

Ventilator 13 is powered by either 120 Volt AC, an internal battery, or an external 12 Volt DC battery. Whichever power source is presently in use is shown by indicator lights 52. A recharge on/off switch 54 is also provided. A speaker 56 provides an audible alarm if the unit switches power source, or if the internal DC power is lost or too low. Fuses 58 and a hospital grade DC connector for the external 12 Volt battery are also provided.

Ventilator 13 provides a number of sensor mechanisms which alarm when certain conditions arise. A sensitivity adjustment dial 62 allows a clinician to determine the amount of inspiratory effort expected from a patient. When the amount is less than expected, speaker 56 will emit an audible alarm. If ventilator 13 does not detect either a spontaneous effort to breathe by the patient or a low pressure setting within 15 seconds, an apnea alarm is sounded by speaker 56.

A low pressure alarm set dial 64 can define the low pressure needed to sound an alarm anywhere between 2 to 50 cm H$_2$O. A high pressure control dial 66 sets the peak pressure needed to sound an alarm from speaker 56 from 10 to 100 cm H$_2$O. A gauge 57 provides a direct air pressure reading for the patient or nurse.

Exhalation valve 24 is controlled by ventilator 13 via exhalation valve control tube 14. Exhalation valve control tube 14 is connected directly between and provides gaseous communication between an exhalation valve outlet 68 on ventilator 13 and a control air inlet 70 on exhalation valve 24. Ventilator 13 utilizes air pressure to move a diaphragm (not shown) inside exhalation valve 24 between an inhalation position and an exhalation position. In the inhalation position, gaseous communication is established directly between tracheotomy connector 28 via outlet 25 and patient air outlet 19 of ventilator 13 via inlet 23.

In the exhalation position, ventilator 13 and the individual's throat no longer are in gaseous communication. Instead, exhalation valve 24 provides gaseous communication between tracheotomy connector 28 via first outlet 25 and the ambient atmosphere via second outlet 30.

It should be understood that the workings of exhalation valve 24 are well known by those skilled in the art and will not be further described herein.

To provide data input to the sensor mechanisms of ventilator 13, sensor tube 16 is mounted at one end to sensor tube opening 71 on exhalation valve-sensor connection 22 mounted proximate to exhalation valve 24. The opposite end of sensor tube 16 is connected to ventilator 13 at sensor tube outlet 72. Sensor tube 16 thus provides gaseous communication between the interior of air tube 12 and ventilator 13. Ventilator 13 monitors the air pressure via sensor tube 16 and sounds an alarm when conditions as previously described occur.

While the above described tubing assembly 11 of the prior art is functional, the use of three separate tubes 12, 14 and 16 is often awkward and sometimes intimidating to set up for patients and nurses. In addition, the use of three separate tubes provides three different items that can be inadvertently disconnected when being carried or moved.

Turning now to FIG. 2, the present invention comprises tubing assembly 10 is shown. As shown in FIGS. 2–4, tubing assembly 10 of the present invention also comprises an air tube 74, an exhalation valve control tube assembly 75 and a sensor tube 16. Exhalation valve control tube assembly 75 sequentially includes a valve-connector tube 85, a first L-shaped portion 86, an internal tube 87, a second L-shaped portion 88 and a connector-ventilator tube 89. As with the prior art, tubes 74, 89 and 16 are of differing sizes to prevent inadvertent mis-connections.

Air tube 74 includes a ventilator-sensor connection 76 which connects at one end to patient air outlet 19 and at a second end to intermediate tube 20, an exhalation valve connection 78 which connects to intermediate tube 20 at one end and to an inlet 23 of an exhalation valve 24 at the opposite end, a second intermediate tube 26 connected at one end to a first outlet 25 of exhalation valve 24 and to a tracheotomy connector 28 at the opposite end.

Turning to FIGS. 3 and 3A, exhalation valve connection 78 is shown in detail. As with the prior art exhalation valve-sensor connection 22, exhalation valve connection 78 connects at one end to intermediate tube 20 and at the other end to inlet 23 of exhalation valve 24. In contrast to the prior art exhalation valve-sensor connection 22, sensor tube opening 71 is not provided in exhalation valve connection 78.

In the preferred embodiment, first L-shaped portion 86 of exhalation valve control tube assembly 75 is formed integrally with exhalation valve connection 78. A nipple 80 extends laterally outward from connection 78 thus forming one leg of first L-shaped portion 86. As best seen in FIGS. 2 and 3A, valve connector tube 85 connects at one end to the control air inlet 70 of exhalation valve 24 and at the other end to nipple 80 of first L-shaped portion 86. Nipple 80 extends through connection 78 where the second leg 81 of first L-shaped portion 86 extends longitudinally opposite exhalation valve 24 towards ventilator-sensor connection 76. One end of internal tube 87 connects to second leg 81.

As best seen in FIGS. 4 and 4A, in the preferred embodiment, ventilator-sensor connection 76 includes a second L-shaped portion 88 intergrally formed therewith. A second nipple 82 forming one leg of second L-shaped portion 88 extends laterally therefrom and to which one end of connector-ventilator tube 89 is connected. From second nipple 82, connector-ventilator tube 89 connects to exhalation valve outlet 68 as in the prior art. Nipple 82 extends through connection 76 where the second leg 83 of second L-shaped portion 88 extends longitudinally towards exhalation valve 24. The second end of internal tube 87 connects to second leg 83. Connectors 76 and 78 allow the greater portion of exhalation valve control tube assembly 75, namely internal tube 87, to be extend longitudinally entirely within intermediate tube 20.

To provide data input to the sensor mechanisms of ventilator 13, sensor tube 16 is mounted at one end to a sensor tube nipple 84 on ventilator-sensor connection 76 mounted proximate to ventilator 13. The opposite end of sensor tube 16 is connected to ventilator 13 at sensor tube outlet 72. Sensor tube 16 thus provides gaseous communication between the interior of air tube 12 and ventilator 13. Ventilator 13 monitors the air pressure via sensor tube 16 and sounds an alarm when conditions as previously described occur.

The operation of the apparatus is identical to that of the prior art described previously and thus will not be repeated herein.

Although only certain embodiments of the invention have been illustrated and described, it will be apparent to those skilled in the art that various changes and modifications may be made therein without departing from the spirit of the invention or from the scope of the appended claims. For example, often ventilator 13 may connect patient air outlet to the inlet of a humidifier or other such device. In which case the ventilator-tubing connection 76 connects at one end to the outlet of the humidifier instead of directly to patient air outlet 19. Tubes 14 and 89 still connect directly to the ventilator.

That which is claimed is:

1. In combination, a tubing assembly between an exhalation valve and a ventilator, the combination comprising:

the ventilator having a patient air outlet, a exhalation valve control outlet and a sensor outlet operatively connected to a sensing mechanism;

the exhalation valve having a first outlet in gaseous communication with a patient's throat, a second outlet in gaseous communication with the ambient atmosphere, an inlet and a control air inlet, the exhalation valve having inhalation position in which gaseous communication is established between the inlet and the first outlet and an exhalation position in which gaseous communication is established between the first outlet and the second outlet, the exhalation valve being switched between the inhalation position and the exhalation position by air pressure exerted at the control air inlet;

an intermediate tube providing gaseous communication between the patient air outlet and the inlet;

an exhalation valve connection attached at one end to the intermediate tube and at the other end to the inlet of the exhalation valve, the exhalation valve connection having a first L-shaped portion formed integrally therewith, the first L-shaped portion having a first leg extending laterally through the exhalation valve connection, the second leg extending longitudinally within the exhalation valve connection in a direction opposite the exhalation valve;

a ventilator-sensor connection attached at one end to the patient air outlet and at the other end to the intermediate tube opposite the exhalation valve connection, the ventilator-sensor connection having a second L-shaped portion formed integrally therewith, and a sensor tube opening therethrough, the second L-shaped connector having a first leg extending laterally through the ventilator-sensor connection, the second leg extending longitudinally within the ventilator-sensor connection in a direction towards the exhalation valve:

a sensor tube connected at one end to the ventilator-sensor connection and at the other end to the sensor outlet providing gaseous communication between the sensor mechanism of the ventilator and the ventilator-sensor connection; and an exhalation valve control tube connected at one end to the control air inlet and at the opposite end to the exhalation valve control outlet providing gaseous communication between the control air inlet and the exhalation valve control outlet whereby the ventilator controls the air pressure at the control air inlet, the exhalation valve control tube extending through the first tube opening, through the intermediate tube and extending through the second tube opening.

2. The assisted breathing apparatus of claim 1 wherein the sensor tube, the exhalation valve control tube and the intermediate tube have different diameters.

3. A tubing assembly for use between an exhalation valve and a ventilator for providing assisted breathing to a patient, the tubing assembly comprising:

an intermediate tube;

an exhalation valve connection attached at one end to the intermediate tube and at the other end to an inlet of an exhalation valve;

a ventilator-sensor connection attached at one end to a patient air outlet of a ventilator and at the other end to the intermediate tube opposite the exhalation valve connection;

a sensor tube connected at one end to the ventilator-sensor connection and at the other end to a sensor outlet on a ventilator providing gaseous communication between a sensor mechanism of a ventilator and the ventilator-sensor connection; and an exhalation valve control tube assembly providing gaseous communication between a control air inlet of an exhalation valve and an exhalation valve control outlet of a ventilator, the exhalation valve control tube assembly extending through the exhalation valve connection, through the intermediate tube and extending through the ventilator-sensor connection; and wherein the exhalation valve control tube assembly further includes a valve-connector tube, a first L-shaped portion, an internal tube, a second L-shaped portion and a connector-ventilator tube, the first L-shaped portion having a first leg extending laterally through the exhalation valve connection and a second leg extending longitudinally within the exhalation valve connection in a direction opposite an exhalation valve, the second L-shaped connector having a first leg extending laterally through the ventilator-sensor connection and a second leg extending longitudinally within the ventilator-sensor connection in a direction towards an exhalation valve, the valve connector tube being attached at one end to the first leg of the first L-shaped portion and at the other end to a control air inlet of an exhalation valve, the opposing ends of the internal tube connected to the second legs of the first and second L-shaped portions, the connector-ventilator tube being connected at one end to the first leg of the second L-shaped portion and at the other end to an exhalation valve control outlet on a ventilator.

4. The tubing assembly of claim 3 wherein the first and second L-shaped portions are formed integrally with the exhalation valve connector and the ventilator-sensor connector, respectively.

* * * * *